United States Patent [19]
Feygin

[11] Patent Number: 6,116,297
[45] Date of Patent: Sep. 12, 2000

[54] ARTICLE COMPRISING A REFILLABLE CAPILLARY TUBE

[75] Inventor: Ilya Feygin, Mountainside, N.J.

[73] Assignee: Pharmacopeia, Inc., Princeton, N.J.

[21] Appl. No.: 09/272,920

[22] Filed: Mar. 19, 1999

Related U.S. Application Data

[63] Continuation-in-part of application No. 08/993,106, Dec. 18, 1997, Pat. No. 5,957,167.

[51] Int. Cl.$^7$ ...................................................... G01F 11/00
[52] U.S. Cl. ................................ 141/31; 141/1; 141/130; 141/284; 422/100; 73/864.02; 73/864.72
[58] Field of Search .................................. 141/1, 31, 130, 141/284; 73/864.02, 864.72; 422/100

[56] References Cited

U.S. PATENT DOCUMENTS

| | | | |
|---|---|---|---|
| 3,358,496 | 12/1967 | Farmer | 73/864.72 |
| 3,536,449 | 10/1970 | Astle | 73/864.72 |
| 3,568,735 | 3/1971 | Lancaster | 141/238 |
| 4,116,637 | 9/1978 | Kitahara | 422/63 |
| 4,260,467 | 4/1981 | Smith et al. | 204/413 |
| 4,309,912 | 1/1982 | Smith | 73/864.72 |
| 4,731,335 | 3/1988 | Brigati | 436/180 |
| 4,939,410 | 7/1990 | Nagy et al. | 204/413 |
| 5,226,462 | 7/1993 | Carl | 141/1 |
| 5,230,864 | 7/1993 | Columbus | 422/100 |
| 5,334,353 | 8/1994 | Blattner | 422/100 |
| 5,456,294 | 10/1995 | Tsao et al. | 141/1 |
| 5,460,782 | 10/1995 | Coleman et al. | 422/100 |
| 5,578,178 | 11/1996 | Nuzzio | 204/413 |
| 5,763,278 | 6/1998 | Sickinger et al. | 436/180 |
| 5,770,151 | 6/1998 | Roach et al. | 422/63 |
| 5,807,522 | 9/1998 | Brown et al. | 422/50 |

*Primary Examiner*—J. Casimer Jacyna
*Attorney, Agent, or Firm*—DeMont & Breyer, LLC; Wayne S. Breyer

[57] ABSTRACT

In one embodiment, the present invention provides an improved liquid dispenser suitable for dispensing a small volume of liquid. The liquid dispenser has a capillary channel suitable for aspirating and retaining a predetermined and repeatable volume of liquid via capillary action. To dispense retained liquid, the capillary channel is accelerated and then abruptly decelerated. Liquid is supplied to the capillary channel via a liquid-supply conduit that is in fluid communication therewith. When the capillary channel is abruptly decelerated during the dispensing operation, liquid within the capillary channel is momentarily "sheared" or separated from liquid within liquid-supply conduit. After such "shearing," liquid flow is reestablished under capillary action, and the emptied capillary channel is thereby refilled. The refilling operation occurs "automatically" and without the need for a repositioning operation (i.e., moving the capillary channel to a liquid reservoir to aspire additional liquid) as in the prior art.

20 Claims, 3 Drawing Sheets

1

ARTICLE COMPRISING A REFILLABLE CAPILLARY TUBE

CROSS-REFERENCE TO RELATED CASES

This application is a continuation-in-part of U.S. pat. application Ser. No. 08/993,106 filed Dec. 18, 1997, now U.S. Pat. No. 5,957,167, and incorporated by reference herein.

FIELD OF THE INVENTION

The present invention relates generally to an article and method for filling/refilling capillary-action devices with liquid.

BACKGROUND OF THE INVENTION

A variety of devices have been developed for transferring and manipulating very small volumes (e.g., on the order of a microliter) of liquid. Such devices typically collect liquid from a reservoir, such as the wells of a microtiter plate, and discharge it at a second site. Collection is usually effected via members that are configured to cause liquid flow via capillary action.

Typical of such devices is a liquid deposition device disclosed in U.S. Pat. No. 5,770,151 to Roach et al. The liquid deposition device disclosed therein includes a tubular liquid deposition member having a hollow cylindrical wall extending from a closed end towards an open end. A longitudinal gap extends from the open end of the cylindrical wall toward the closed end. The cylindrical wall, hereinafter "capillary member," defines a lumen wherein both the lumen and the longitudinal gap are adapted to facilitate capillary action of liquid in fluid communication therewith.

The tubular liquid deposition member is filled with liquid by contacting the open end of the capillary member with liquid that resides in one of number of reservoirs or wells. Liquid moves into the lumen of the capillary member from the well via capillary action. According to the patent, the longitudinal gap facilitates rapid influx of liquid into the lumen by allowing air that is present therein to rapidly exhaust as liquid moves up the capillary member. To dispense the collected liquid, the open end of the capillary member is brought into contact with a surface. After dispensing its liquid charge, the capillary member can be refilled for a subsequent dispensing operation by moving the capillary member to a well and repeating the collection operation.

Some liquid handling applications require repeated collection/dispensing cycles. In such applications, each subsequent cycle requires: (1) moving the capillary member from the dispensing site of a previous cycle to a reservoir/collection site for refilling, (2) refilling the capillary member, (3) moving the capillary member from the collection site to a dispensing site, and (4) dispensing the collected liquid. Alternatively, the deposition and collection sites can be moved to the capillary tube. In either scenario, the time required to collect liquid, including the two repositioning steps (1) and (3), accounts for a substantial portion of the overall collection/dispensing cycle time. As some applications require thousands of such liquid handling cycles, the inefficiency of the aforedescribed refilling operation results in a significant time penalty and is a significant drawback of such conventional liquid deposition devices.

As such, the art would benefit from a device and method that reduces the time required to refill a capillary member.

SUMMARY OF THE INVENTION

In some embodiments, the present invention provides an improved liquid dispenser suitable for dispensing a small volume of liquid. In one embodiment, the present liquid dispenser comprises a capillary channel suitable for collecting and retaining a predetermined and repeatable volume of liquid via capillary action. To dispense retained liquid, the capillary channel is accelerated and then abruptly decelerated. The inertia of the accelerated liquid overcomes capillary forces that would otherwise retain the liquid in the capillary channel. As a result, liquid is dispensed from a dispensing end of the capillary channel.

Liquid is delivered to the capillary channel via a liquid-supply conduit that is in fluid communication therewith at a first region remote from the dispensing end. When the capillary channel is abruptly decelerated during the dispensing operation, liquid within the capillary channel is "sheared" or separated from liquid within the liquid-supply conduit. Such shearing is due to the action of a liquid interrupt. In one embodiment, the liquid interrupt is realized as an abrupt direction change in liquid flow between the liquid-supply conduit and the capillary channel.

The interruption of liquid flow between the liquid-supply conduit and the capillary channel is transitory; the liquid flow is reestablished substantially instantaneously after deceleration. Under capillary action, liquid again flows from the liquid-supply conduit to the capillary channel, refilling the empty capillary channel. In such a manner, the capillary channel is "automatically" refilled after the dispensing operation without the need for repositioning operations as in the prior art.

DETAILED DESCRIPTION

Figure 7:
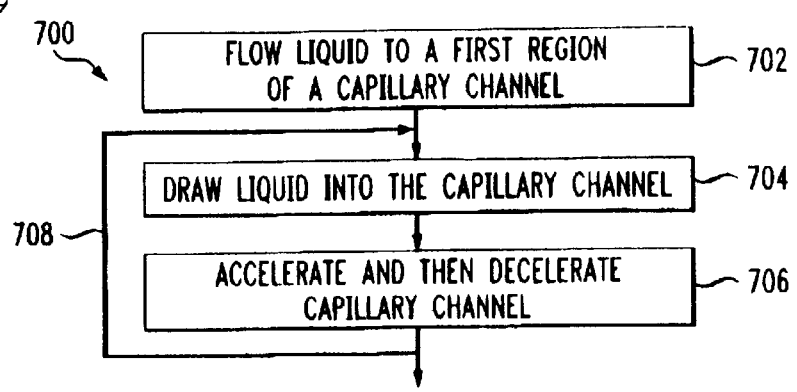
FIG. 7 depicts, via flow diagram, a method in accordance with an illustrated embodiment of the present invention.

In one embodiment, the present invention provides an improved method for dispensing small volumes of liquid. An illustrative embodiment of a method 700 in accordance with the present teachings is illustrated by flow diagram in FIG. 7. According to operation 702 of method 700, liquid is flowed (e.g., through a conduit) to a first region of a capillary channel. As defined herein, a capillary channel is any structure (e.g., parallel plates, cylindrical wall, etc.) that is capable of collecting/aspirating liquid via capillary action. As indicated in operation 704, a predetermined and repeatable volume of that liquid is drawn into the capillary channel at the first region via capillary action. The capillary channel is accelerated and then rapidly decelerated, as per operation 706. Upon such abrupt deceleration, the liquid present in the capillary channel is dispensed from a second region thereof and additional liquid is drawn into the capillary channel at the first region. In such a manner, the capillary channel is automatically and immediately refilled, as indicated by loop back 708, for a subsequent dispensing operation without moving the capillary channel to a liquid reservoir or vice versa.

A liquid dispenser 100 in accordance with an illustrated embodiment of the present invention, and suitable for carrying out the improved dispensing method described above, is depicted in FIG. 1. Illustrative dispenser 100 includes two liquid-dispensing members 102. Each liquid-dispensing member 102 includes a capillary channel 104 suitable for collecting and retaining a predetermined volume of liquid. Capillary channel 104 depends from a body portion 120 that is operatively connected to an actuator 128. Actuator 128 is operable to accelerate and abruptly decelerate liquid-dispensing members 102.

In illustrative dispenser 100, capillary channels 104 comprise spaced-apart, coextensive, elongate members 106*a* and 106*b*. In some embodiments, elongate members 106*a*/*b* taper toward a discharge or dispensing end 112 of capillary channel 104. A gap 114 between elongate members 106*a*/*b*, and the width of such elongate members, are suitably selected to allow collection and retention of a chosen liquid via capillary action. A gap 114 in the range of about 1 to about 1.5 millimeters (mm), and elongate members 106*a*/*b* having a width of about 1 mm or more are expected to create a capillary effect in conjunction with a wide variety of liquids. The length, l, of elongate members 106*a*/*b* is suitably selected, in view of the aforedescribed dimensions, such that each capillary channel 104 is capable of retaining a liquid volume in the range of about 0.5 to about 5 microliters.

In one embodiment, opposed surfaces 108 and 110 of respective elongate members 106*a* and 106*b* are concave. Such concave opposed surfaces can be obtained, for example, by forming a slit in a capillary tube. In a second embodiment, opposed surfaces 108 and 110 are substantially flat. Such flat opposed surfaces can be obtained, for example, by forming a slit in a solid rod.

A liquid-supply conduit 122 (shown only on one of liquid-dispensing members 102 for clarity of illustration) is in fluid communication with each capillary channel 104 at a region or interface 124. Liquid is drawn from liquid-supply conduit 122 into capillary channel 104 via capillary action. In some embodiments, a discontinuity, disruption or other change in gap 114 or elongate surface(s) 106*a*/*b* is provided to terminate the capillary action of capillary channel 104. Such a discontinuity/disruption facilitates aspiring a predetermined and repeatable volume of liquid. In illustrative capillary channels 104, the discontinuity is a "widening" 118 in gap 114. Fluid communication between liquid-supply conduit 122 and capillary channel 104 is advantageously effected near widening 118 (or other discontinuity, etc., for terminating capillary action).

As indicated in the description of method 700, the small volume of liquid that is collected in each capillary channel 104 is dispensed therefrom by accelerating, and then abruptly decelerating, liquid-dispensing members 102. The inertia of accelerated liquid within capillary channel 104 overcomes capillary forces holding the liquid within the abruptly decelerated capillary channel. As such, the liquid escapes from capillary channel 104.

Actuator 128 accelerates and decelerates liquid-dispensing members 102. It will be appreciated by those skilled in the art that a wide variety of actuator configurations may suitably be used in conjunction with the present invention for such purpose. One of such configurations is described in detail later in this specification and illustrated in FIG. 6.

Differences in dimensions between surfaces 108 and 110 of respective elongate members 106*a* and 106*b*, or between surface characteristics of such surfaces, may result in local variations in surface tension. Such local variations may cause a deviation in the course of liquid issuing from capillary channel 104 of liquid-dispensing member 102. To reduce or eliminate any such deviation for those or other reasons, liquid-dispensing members 102 advantageously include, in some embodiments, a liquid director 126. For clarity of illustration, liquid director 126 is depicted on only one of the liquid-dispensing members. Configured as a "needle-like" structure in the embodiment shown in FIG. 1, liquid director 126 is located within gap 114. In the illustrated embodiment, liquid director 126 extends beyond elongated members 106a/b.

During the dispensing process, the dispensable volume of liquid slides along liquid director 126 forming a symmetrical droplet due to surface tension. The liquid, after disassociating with liquid director 126, maintains a substantially straight-line course out of capillary channel 104. It should be understood that a liquid director having a different physical configuration, as may be devised by those skilled in the art, and operable to direct a small volume of liquid in a predetermined direction, may suitably be used in place of the aforedescribed structure.

In accordance with the present teachings, illustrative dispenser 100 further includes a liquid interrupt that momentarily disrupts the flow of liquid from liquid-supply conduit 122 to the capillary channel 104 when the liquid within the capillary channel is dispensed. In the illustrative embodiment depicted in FIG. 1, the liquid interrupt is realized as an abrupt change in the direction of liquid flowing from the liquid-supply conduit 122 to capillary channel 104. The abrupt change occurs at interface 124 between liquid-supply conduit 122 and capillary channel 104. In particular, the direction of flow of liquid within liquid-supply conduit 122 at interface 124 is indicated by axis 1—1. The direction of flow of liquid within capillary channel 104 (when dispensed) is indicated by axis 2—2. The change in direction of flow is described by non-zero angle, $\alpha$, which is the included angle between the axes 1—1 and 2—2.

As a result of the abrupt change in flow direction at interface 124, liquid within capillary channel 104 is "sheared" or separated from liquid within liquid-supply conduit 122 when liquid-dispensing members 102 are abruptly decelerated during the dispensing operation. Such separation or interruption is momentary; the liquid flow from liquid-supply conduit 122 into capillary channel 104 is reestablished substantially instantaneously after deceleration. Since the liquid comprising the reestablished flow has been decelerated, it does not possess the inertia required to escape the capillary channel 104. In such a manner, capillary channel 104 is "automatically" refilled following the dispensing operation without the need for a repositioning operation as in the prior art.

FIGS. 2–5 depict several illustrative arrangements of a capillary channel, liquid-supply conduit, liquid interrupt and liquid director in accordance with the present teachings. Such arrangements depict some of the ways in which the liquid-supply conduit and liquid interrupt described herein can be used in conjunction with capillary channels to provide improved liquid dispensers in accordance with an illustrated embodiment of the present invention. Undoubtedly, configurations other than those depicted in FIGS. 2–5 that are suitable for creating a capillary channel will occur to those skilled in the art. A liquid-supply conduit and liquid interrupt as described herein may suitably be used with such other configurations to provide an improved liquid dispenser in accordance with the present teachings.

Figure 2:
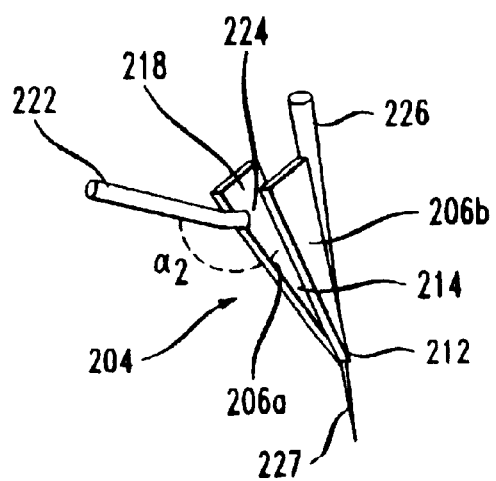
FIG. 2 depicts a first embodiment of a capillary channel, liquid-supply conduit, liquid interrupt and liquid director in accordance with the present teachings.

In FIG. 2, illustrative capillary channel 204 comprises two spaced-apart, coextensive, flat, tapering elongate members 206a and 206b. Elongate members 206a and 206b are not parallel to one another; rather, gap 214 widens with distance from dispensing end 212. At region 218, elongate members 206a/b are sufficiently far apart to terminate capillary action. Liquid-supply conduit 222 is in fluid communication with capillary channel 204 at interface 224 in region 218. There is an abrupt change in flow direction at interface 224, as illustrated by angle $\alpha_2$.

At least a portion of liquid director 226 is disposed within gap 214 between elongated members 206a/b. Tip 227 of liquid director 226 extends beyond dispensing end 212 of capillary channel 204 to direct dispensed liquid in a desired direction.

Figure 3:
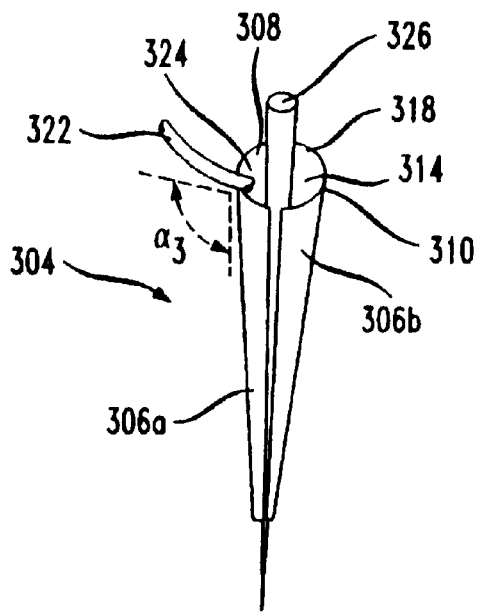
FIG. 3 depicts a second embodiment of a capillary channel, liquid-supply conduit, liquid interrupt and liquid director in accordance with the present teachings.

In FIG. 3, illustrative capillary channel 304 comprises two spaced-art, coextensive, curved elongate members 306a and 306b. Liquid director 326 is disposed between elongate members 306a/b along a centrally-located long-axis of capillary channel 304. Capillary action is developed between liquid director 326 and inner surfaces 308 and 310 of respective elongate members 306a and 306b. Gap 314 between elongate members 306a/b and liquid director 326 widens until, at a region 318, capillary action ceases. Liquid-supply conduit 322 is in fluid communication with capillary channel 304 at interface 324 in region 318. An abrupt change in flow direction is indicated at interface 324 by angle $\alpha_3$.

Figure 4:
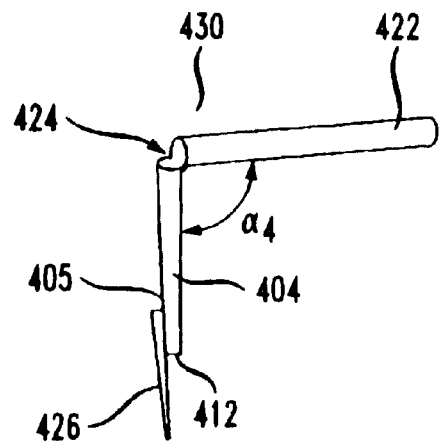
FIG. 4 depicts a third embodiment of a capillary channel, liquid-supply conduit, liquid interrupt and liquid director in accordance with the present teachings.

In the embodiment depicted in FIG. 4, illustrative capillary channel 404 and liquid-supply conduit 422 comprise two different regions of a single conduit 430. Conduit 430 is cut and bent at a site 424, which functionally divides conduit 430 into capillary channel 404 and liquid-supply conduit 422. Site 424 is the interface between liquid-supply conduit 422 and capillary channel 404. An abrupt change in flow direction is indicated at interface 424 by angle $\alpha_4$. Liquid director 426 is disposed adjacent to exterior surface 405 of capillary channel 404 and extends beyond dispensing end 412 thereof.

Figure 5:
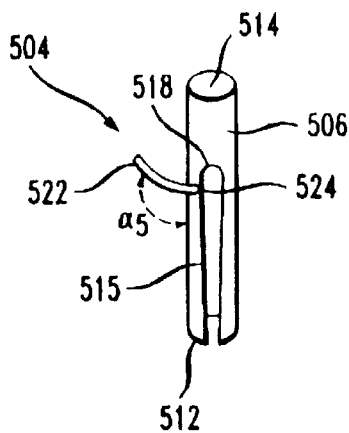
FIG. 5 depicts a fourth embodiment of a capillary channel, liquid-supply conduit, liquid interrupt and liquid director in accordance with the present teachings.

In the illustrative embodiment of FIG. 5, capillary channel 504 comprises a cylindrical wall 506 defining a lumen 514. Cylindrical wall 506 includes a longitudinal slit 515 that extends from dispensing end 512 towards a terminus 518. Longitudinal slit 515 widens along its length toward terminus 518. Liquid-supply conduit 522 is in fluid communication with capillary channel 504 at interface 524 near terminus 518. An abrupt change in flow direction is indicated at interface 324 by angle $\alpha_5$.

Figure 6:
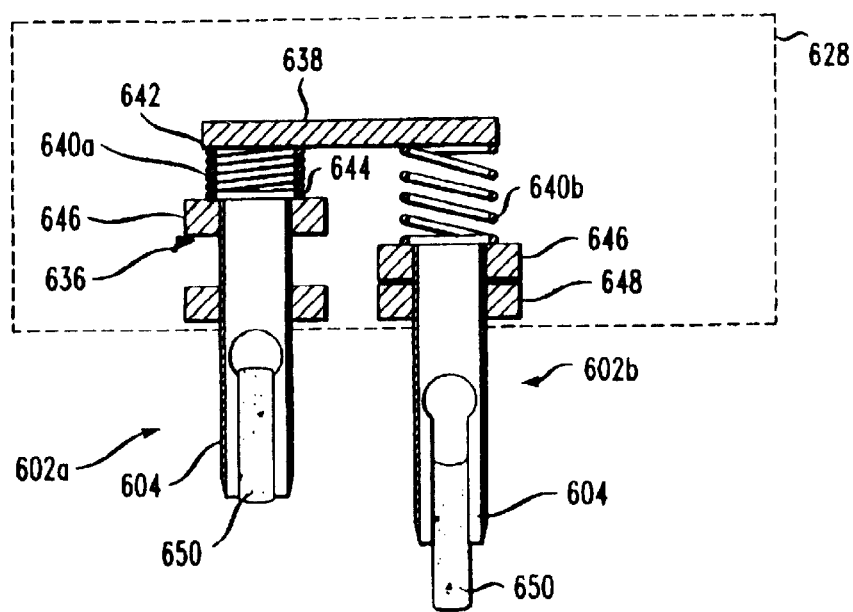
FIG. 6 depicts an illustrative embodiment of an actuator suitable for use in conjunction with the present invention.

An illustrative embodiment of an actuator 628 operable to accelerate and rapidly decelerate liquid-dispensing members 602 is depicted in FIG. 6. In the embodiment shown in FIG. 6, the actuator 628 comprises a biasing member configured as helical springs 640a/b, a movable stop member 646 and a fixed stop member 648.

Each helical spring 640a/b is attached, at a first end 642, to a rigid base 638, and is further attached at a second end 644 to one of the liquid-dispensing members 602a/b. To develop energy for accelerating liquid-dispensing members 602a/b, the springs are placed in a compressed state. Spring 640a is depicted in the compressed state. Spring 640a is maintained in such a compressed state using, for example, a latch 636. To dispense liquid 650 from capillary channels 604, latch 636 is released, allowing the springs 640a/b to expand thereby releasing stored energy. As a result, the attached liquid-dispensing members 602a/b are accelerated in the direction of expansion.

Before an expanding spring, such as the spring 640b, is restored to a fully uncompressed state, movable stop member 646 contacts fixed stop member 648, halting expansion of the spring and abruptly decelerating depending liquid-dispensing member 602b. The abrupt deceleration of liquid-dispensing member 602b causes liquid 650 retained in capillary channel 604 to dispense.

In the illustrative embodiment depicted in FIG. 6, actuator 628 comprises a relatively simple arrangement of springs and stops. In other embodiments, the actuator utilizes more sophisticated pneumatic, hydraulic or electrodynamic systems. Several other actuating arrangements are described in U.S. Pat. App. Ser. No. 08/993,106.

Figure 1:
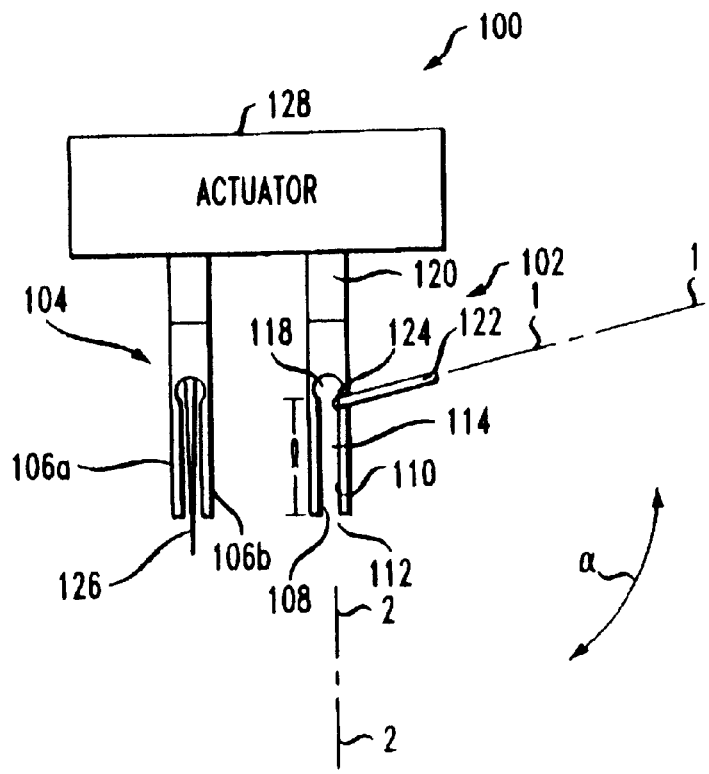
FIG. 1 depicts a liquid dispenser in accordance with the illustrated embodiment of the present invention.

In the dispensers depicted in FIGS. 1 and 6, only two liquid-dispensing tubes are depicted. In other embodiments, a greater number of such capillary channels are present. For example, one embodiment of a liquid dispenser advantageously incorporates ninety-six capillary channels. Such a dispenser is particularly useful in conjunction with liquid transfer to and from a ninety-six-well microtiter plate. In another embodiment particularly useful in conjunction with ninety-six well microtiter plates, the liquid dispenser includes eight capillary channels. As a ninety-six-well microtiter plate is typically arranged in twelve columns of eight wells each, such a plate is advantageously serviced in 12 cycles by an eight-capillary-channel device. And, while perhaps of less utility, the present dispenser can also incorporate a single liquid-dispensing tube.

Although specific embodiments of this invention have been shown and described herein, it is to be understood that these embodiments are merely illustrative of the many possible specific arrangements that can be devised in application of the principles of the invention. Numerous and varied other arrangements can be devised in accordance with these principles by those of ordinary skill in the art without departing from the scope and spirit of the invention.

I claim:

1. An article comprising:
    a capillary channel operable, via capillary action, to retain an amount of liquid;
    a conduit in fluid communication with the capillary channel, the conduit operable, in conjunction with the capillary channel, to deliver the amount of liquid to the capillary channel; and
    an interface between said conduit and said capillary channel, said interface operative to disrupt liquid flow from the conduit to the capillary channel under rapid deceleration.

2. The article of claim 1 wherein there is a change of direction in liquid flow at said interface.

3. The article of claim 2, wherein an included angle between the conduit and a portion of the capillary channel between the interface and a dispensing end of the capillary channel is less than 180 degrees.

4. The article of claim 1, and further comprising:
    a liquid director physically configured to substantially eliminate deviations in a desired path followed by liquid dispensed from the capillary channel.

5. The article of claim 4, wherein the physical configuration of the liquid director is substantially needle-like.

6. The article of claim 5, wherein the liquid director extends beyond a dispensing end of the capillary channel.

7. The article of claim 5, wherein the liquid director is aligned with a centrally-located long axis of the capillary channel.

8. The article of claim 4 wherein there is a change of direction in liquid flow at said interface.

9. The article of claim 8, wherein an included angle between the conduit and a portion of the capillary channel between the interface and a dispensing end of the capillary channel is less than 180 degrees.

10. The article of claim 1, and further comprising:

an actuator operable to accelerate and then abruptly decelerate the capillary channel, wherein upon abrupt deceleration, the liquid retained by the capillary channel is dispensed therefrom.

11. The article of claim 10, wherein the actuator comprises:

a biasing member operable to store energy in a first position, wherein, when released from the first position, a portion of the stored energy is converted to kinetic energy thereby accelerating at least a part of the biasing member and also accelerating the capillary channel, which is in mechanical communication therewith.

12. The article of claim 11, wherein the actuator further comprises:

a first and a second stop, wherein the first stop is substantially nonmovable and the second stop is mechanically linked to the capillary channel and thereby accelerated therewith, and, wherein, the first stop is suitably positioned to engage the second stop after the second stop has moved a predetermined distance as a result of said acceleration, wherein, the capillary channel is abruptly decelerated when the first and second stops engage.

13. The article of claim 12 wherein the first stop is positioned to engage the second stop before substantially all stored energy available for conversion into kinetic energy is so converted.

14. The article of claim 11, wherein the biasing member is a spring.

15. The article of claim 1, wherein the capillary channel comprises: spaced-apart, coextensive, elongate members.

16. The article of claim 15, wherein the elongate members taper toward a dispensing end of the capillary channel.

17. The article of claim 15 wherein the elongate members are flat.

18. The article of claim 15 wherein the elongate members are curved.

19. The article of claim 1, wherein the capillary channel comprises:

a cylindrical wall defining a lumen, the cylindrical wall including a longitudinal gap that extends from a dispensing end towards a second end.

20. A method for filling, dispensing and then refilling a capillary channel comprising:

flowing liquid toward a first region of the capillary channel from a conduit that is in fluid communication therewith;

changing a direction of liquid flow at an interface between said conduit and said first region of said capillary channel;

drawing an amount of the liquid into the capillary channel at the first region via capillary action; and accelerating and then abruptly decelerating the capillary channel.

* * * * *